United States Patent [19]

Shimmick

[11] Patent Number: 5,713,892
[45] Date of Patent: Feb. 3, 1998

[54] METHOD AND APPARATUS FOR COMBINED CYLINDRICAL AND SPHERICAL EYE CORRECTIONS

[75] Inventor: John K. Shimmick, Redwood City, Calif.

[73] Assignee: Visx, Inc., Santa Clara, Calif.

[21] Appl. No.: 138,552

[22] Filed: Oct. 15, 1993

Related U.S. Application Data

[63] Continuation of Ser. No. 746,446, Aug. 16, 1991, abandoned.

[51] Int. Cl.$^6$ .................................................. A61N 5/06
[52] U.S. Cl. ............................... 606/5; 606/10; 606/13; 606/17
[58] Field of Search ........................ 606/2–6, 10–13, 606/17–19

[56] References Cited

U.S. PATENT DOCUMENTS

| | | | |
|---|---|---|---|
| 4,665,913 | 5/1987 | L'Esperance, Jr. | 606/5 |
| 4,669,466 | 6/1987 | L'Esperance, Jr. | 606/5 |
| 4,729,372 | 3/1988 | L'Esperance, Jr. | 606/5 |
| 4,732,148 | 3/1988 | L'Esperance, Jr. | 606/5 |
| 4,770,172 | 9/1988 | L'Esperance, Jr. | 606/5 |
| 4,773,414 | 9/1988 | L'Esperance, Jr. | 606/5 |
| 4,838,266 | 6/1989 | Kozoil et al. | 606/5 |
| 4,911,711 | 3/1990 | Tebaur | 606/5 |
| 4,994,658 | 2/1991 | Raven et al. | 606/5 |

OTHER PUBLICATIONS

Photorefractive Keratectomy: A Technique for Laser Refractive Surgery; Munnerlyn et al., J. Cataract Refract Surg., vol. 18, pp. 46–52 (Jan. 1988).

Excimer Laser Surgery of the Cornea, Trokel et al. Am. J. Ophthalmology, 96: 710–715 (1983).

Application of the Excimer Laser to Area Recontouring of the Cornea; Yoder. et al, SPIE vol. 1023, Excimer Laser and Applications, pp. 260–267 (1988).

Photorefractive Keratectomy to Create Toric Ablations for Correction of Astigmatism, Arch Ophterce (MO), vol. 109, May, 1991, pp. 710–713, McDonnell et al.

*Primary Examiner*—David M. Shay
*Attorney, Agent, or Firm*—Townsend and Townsend and Crew LLP

[57] ABSTRACT

A method for performing concurrent spherical and cylindrical corrections to the corneal surface of the eye to reduce myopia and astigmatism. A laser beam irradiates the corneal surface via a variable diameter iris and a slot produced by a pair of translatable blades. The width of the slot and the diameter of the iris are varied as the laser is pulsed to produce a toric ablation of the corneal surface. Alternatively, the laser beam is passed through a succession of apertures in a tilted variable aperture element to produce toric ablation. The total number of laser pulses required to effect both types of correction is equal to the number required for the spherical correction alone, reducing the laser power and the procedure time. The toric ablation produces no steep end walls as with standard cylindrical ablation procedures, thereby eliminating hyperopic shift and minimizing flattening along the ablated cylinder axis.

12 Claims, 2 Drawing Sheets

METHOD AND APPARATUS FOR COMBINED CYLINDRICAL AND SPHERICAL EYE CORRECTIONS

This application is a continuation of application Ser. No. 07/746,446 filed Aug. 16, 1991, now abandoned.

BACKGROUND OF THE INVENTION

This invention relates to ophthalmological surgery techniques which employ an ultraviolet laser used to provide photodecomposition of the surface of the cornea in order to correct vision defects.

Ultraviolet laser based systems and methods are known for enabling ophthalmological surgery on the surface of the cornea in order to correct vision defects by the technique known as ablative photodecomposition. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; and U.S. patent application Ser. No. 081,986 filed Aug. 5, 1987 for "PHOTOREFRACTIVE KERATECTOMY".

In the above-cited U.S. Pat. No. 4,665,913 several different techniques are described which are designed to effect corrections for specific types of optical errors in the eye. For example, a myopic condition, which is typically caused by excessive curvature in the anterior surface of the cornea, is corrected by laser sculpting the corneal surface to flatten the curvature. In addition, an astigmatic condition, which is typically caused by a cylindrical component of curvature departing from the otherwise generally spherical curvature of the surface of the cornea, is corrected by effecting cylindrical ablation about the axis of cylindrical curvature of the eye. Other optical errors can be corrected in a similar fashion.

The technique for providing the flattening of the corneal curvature for myopia error correction involves selectively varying the area of the cornea exposed to the laser beam radiation to produce an essentially spherical surface profile of reduced curvature. This selective variation of the irradiated area may be accomplished in a variety of ways. U.S. Pat. No. 4,732,148 cited above discloses the technique of providing a movable opaque element having apertures of various diameters and passing the laser beam through different ones of the apertures in a programmed fashion, starting either with a smallest diameter aperture and progressively increasing the surface area of exposure using apertures of wider diameters, or using the reverse process. Another technique for accomplishing varying areal exposure employs a variable diameter iris for controlling the area of the cornea exposed to the laser beam. Still another technique for providing the flattening of the corneal curvature for myopia error correction involves the use of a laser beam attenuator which varies the energy distribution of the laser beam to sculpt the surface of the cornea in conformance with the varied energy distribution. The attenuator typically includes a positive lens-shaped portion with a laser energy absorbing material and end caps having planar outer surfaces and the same refractive index as the positive portion, which prevents refraction of the laser beam upon passing through the attenuator. This technique is disclosed in U.S. Pat. No. 4,838,266, issued Jun. 13, 1989 for "LENS SHAPING DEVICE USING A LASER ATTENUATOR", the disclosure of which is hereby incorporated by reference. The astigmatic cylinder correction is typically performed by providing a pair of movable blades which intercept the laser beam and permit only a rectangular area of the cornea to be exposed to the beam through the width of the slit formed by the confronting edges of the blades, and by controlling the width of the slit in a predetermined manner so that a rectangular area of the cornea of either increasing or decreasing width is exposed to the laser beam. The '466 U.S. patent noted above discloses such a variable width slit mechanism.

In practice, the laser sculpturing ophthalmological surgical system is typically provided with delivery system optics which include both the variable diameter beam shaping element and the variable width slit mechanism in order to afford both myopia and astigmatism corrections. In some patients, there are both myopia and astigmatism defects in the same eye, requiring correction of both errors in order to improve vision. In the past, such compound errors have been corrected in systems having a variable diameter element and a variable width slit mechanism in a sequential fashion, with the astigmatic correction typically being performed first with the slit mechanism, followed by the correction for myopia using the variable diameter element. This has the disadvantage that the length of the operation is maximized, which increases the time that the patient's eye must be completely immobilized. This increases the physical strain and stress on the patient.

In addition, the cylindrical ablations required to correct astigmatic errors normally result in sharp transitions in the cornea at the extreme ends of the sculpted area. It has been observed that the eye responds to such sharp transitions by promoting growth of the epithelium and the stroma to smooth out sharp edges in the surface of the cornea. This has an adverse optical effect, sometimes termed the "hyperopic shift", which causes vision regression and thus reduces the effectiveness of the laser sculpting technique. In addition, such sharp transitions have the potential to induce changes in corneal curvature, such as flattening along the cylindrical axis of ablation. In the past, attempts have been made to reduce the hyperopic shift by laser sculpting smoothing transition zones. This has been accomplished by manipulating the diameter of a circular aperture at the ends of the slit to form sigmoidal or "s" shaped transition zones. However, therapeutic patients undergoing large area ablations still exhibit hyperopic shifts.

SUMMARY OF THE INVENTION

The invention comprises a method and apparatus for providing both spherical myopic and cylindrical astigmatic corrections to the cornea of an eye which eliminates the sharp transitions at the ends of the cylindrical ablation and which reduces the time required to perform both types of optical error correction.

From a method standpoint, the invention comprises the steps of concurrently correcting myopic sphere and astigmatic cylinder errors in an eye by selective ultraviolet radiation and ablative photodecomposition of the corneal surface in a volumetric removal of corneal tissue and with depth penetration into the stroma to effect toric ablation. The toric ablation is effected by passing the ultraviolet radiation in the form of a laser beam through a slit of varying width and an aperture of varying diameter. Preferably, the slit width is varied from a minimum value to a maximum value, while the aperture diameter is contemporaneously varied from a maximum value to a minimum value. The inverse operation of the slit and the aperture is also effective, though less preferred. Alternatively, the toric ablation is effected by passing the ultraviolet radiation in the form of a laser beam through a variable aperture modulator to produce an elliptical beam profile of variable dimensions. The elliptical beam profile is preferably produced in this embodiment by angularly directing the laser beam at a variable aperture element having a plurality of circular apertures of different diameters, and progressively positioning different ones of the apertures into the path of the beam. The laser beam encounters a series of elliptical apertures of varying axial dimension, depending on the tilt angle and the aperture diameter.

In another method aspect, the invention comprises a method of changing the anterior surface of the cornea of an eye from initial spherical and cylindrical curvature having myopic and astigmatic optical properties to a subsequent curvature having correctively improved optical properties, which method comprises exposing the surface of the cornea and passing ultraviolet laser radiation through a variable aperture element to selectively ablate the exposed surface of the cornea by photodecomposition, with penetration into the stroma and substantially simultaneous spherical and cylindrical volumetric sculpturing removal of corneal tissue to such penetration depth and profile as to characterize the anterior surface of the cornea with said subsequent curvature.

In a still further aspect of the invention, the invention comprises a method of using an ultraviolet laser to concurrently correct myopic and astigmatic optical errors of an eye, which method comprises the steps of adjusting the intensity of laser beam projection to a level at which laser beam projection onto the exposed surface of the cornea of the eye will result in a corneal tissue ablation per unit time which is a function of a predetermined maximum ablation depth into the stroma of the cornea, and directing the laser beam at the exposed surface of the cornea in a controlled program of circular and rectangular area coverage as a function of time to redefine the exposed surface curvature by volumetric removal of corneal tissue in the course of selective ablative sculpture of the stroma. The step of directing the laser beam at the exposed surface of the cornea is performed by passing the laser beam through an aperture and a slit and varying the diameter of the aperture and the width of the slit to effect toric ablation of the stroma.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
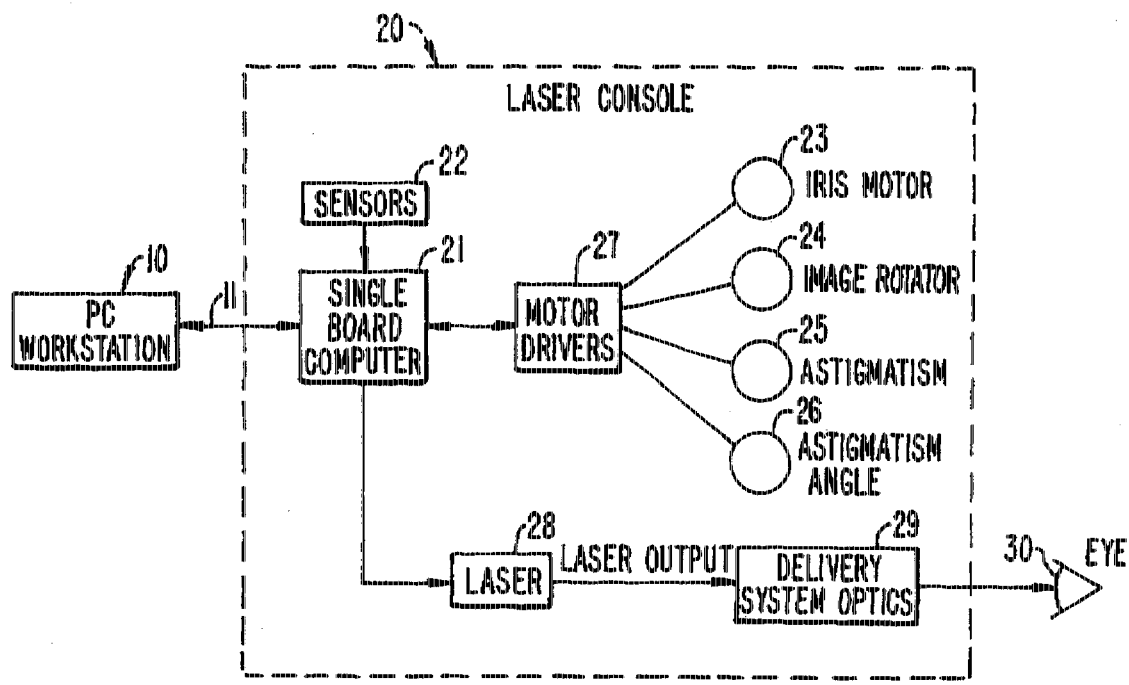
FIG. 1 is a block diagram of an ophthalmological laser surgery system for performing the invention.

Turning now to the drawings, FIG. 1 illustrates a block diagram of an ophthalmological surgery system for performing the invention. As seen in this Fig., a personal computer (PC) work station 10 is coupled to a single board computer 21 of a laser surgery unit 20 by means of a first bus connection 11. PC work station 10 and the subcomponents of laser surgery unit 20 are known components and preferably comprise the elements of the VISX TWENTY/TWENTY EXCIMER LASER SYSTEM available from Visx, Incorporated of Sunnyvale, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, and astigmatism motor 25 and an astigmatism angle motor 26. The feedback signals from sensors 22 are provided via appropriate signal conductors to the single board computer 21, which is preferably an STD bus compatible single board computer using a type 8031 microprocessor. The single board computer 21 controls the operation of the motor drivers generally designated with reference numeral 27 for operating the elements 23–26. In addition, single board computer 21 controls the operation of the Excimer laser 28, which is preferably an argon-fluorine laser with a 193 nanometer wavelength output designed to provide feedback stabilized fluence of 160 mJoules per $cm^2$ at the cornea at the patient's eye 30 via the delivery system optics generally designated with reference numeral 29. Other ancillary components of the laser surgery system 20 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 10.

Figure 2:
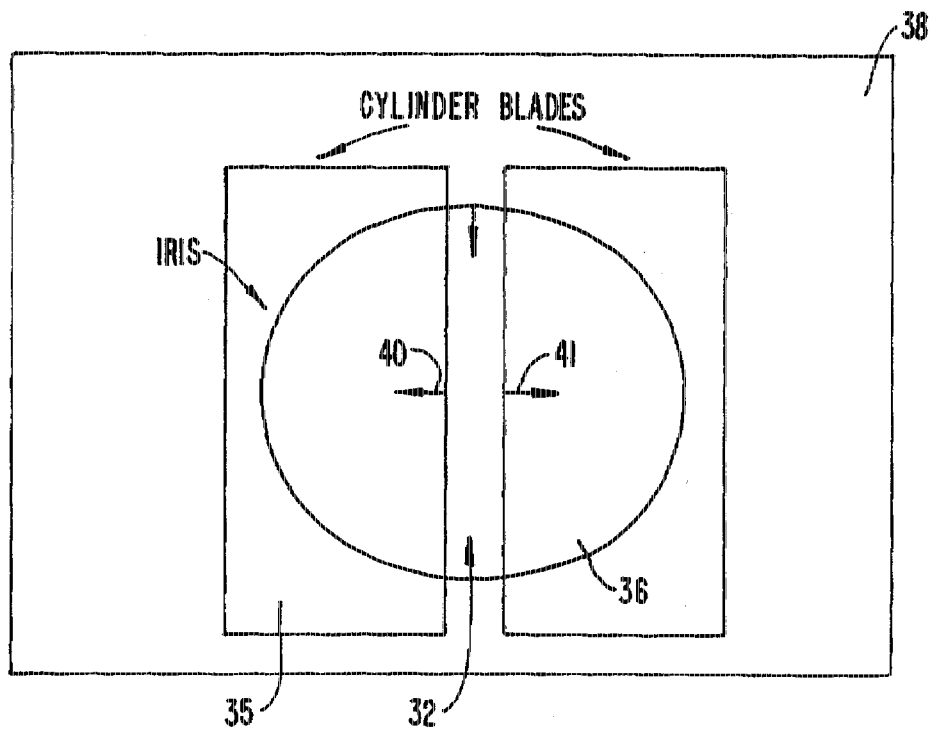
FIG. 2 is a schematic plan view showing the movable slit and variable diameter aperture.

The iris motor 23 is used to control the diameter of a variable diameter iris schematically depicted in FIG. 2. The astigmatism motor 25 is used to control the separation distance between a pair of cylinder blades 35, 36 which are mounted on a platform 38 for bi-directional translatory motion in the direction of arrows 40, 41. Platform 38 is rotatably mounted on a second platform (not illustrated) and is rotationally driven by astigmatism angle motor 26 in a conventional way in order to enable alignment of the slit axis (illustrated in a vertical orientation in FIG. 2) with the cylinder axis of the patient's eye. Iris 32 is driven by iris motor 23 in a known way to change the diameter of the iris opening from a fully opened position (the position illustrated in FIG. 2) to a fully closed position in which the aperture is closed to a minimum diameter of 0.8 min. It is understood that the variable diameter iris 32 and the cylinder blades 35, 36 are positioned with respect to the output of laser 28 in such a manner as to intercept the beam prior to irradiation of the corneal surface of the patient's eye 30. For the purpose of this application, it may be assumed that iris 32 and cylinder blades 35, 36 are part of the delivery system optics subunit 29 shown in FIG. 1.

Figure 3:
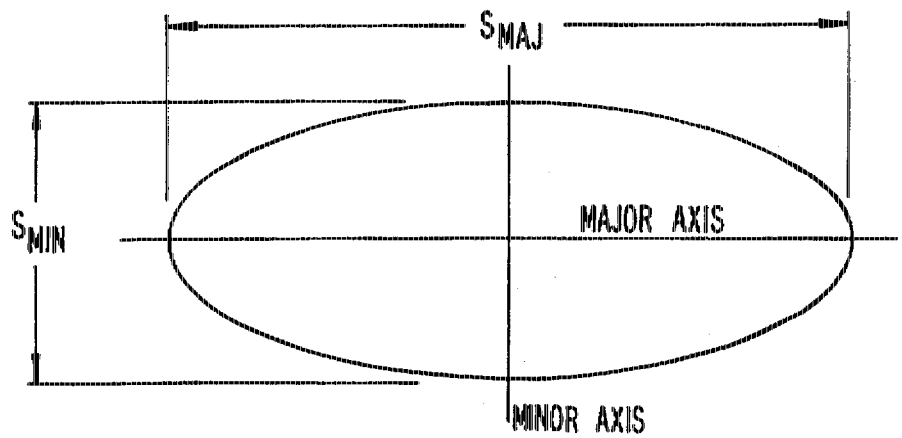
FIG. 3 is a schematic diagram illustrating the geometry of an elliptical ablation.

The system of FIGS. 1 and 2 is used according to the invention to concurrently effect myopic spherical and astigmatic cylindrical corrections to the surface of the cornea by toric ablation. Toric ablation is effected by controlling the combined movement of the cylinder blades 35, 36 and iris 32 over a desired range of movement. The constant depth contour map of a toric ablation consists of a series of concentric ellipses. As seen in FIG. 3, the contour of the outer edge of such an ablation in a flat surface is an ellipse. The ablation geometry along the major and minor axes of the ellipse is spherical, and the ablation has both spherical and cylindrical refractive power.

The refractive power of an elliptical ablation for treating myopia and myopic cylinder is most easily understood using minus notation for the cylinder. The cylinder axis is located along the major axis of the ellipse, while the refractive power of the cylinder is located along the minor axis. For such an ablation in a flat surface, the spherical refractive power can be calculated from the central depth of ablation, the length of the major axis and the index of refraction of the ablated material. The refractive power along the minor axis can similarly be calculated from the length of the minor axis, the depth of ablation and the index of refraction of the ablated material. The cylindrical power can then be calculated by subtracting the refractive (spherical) power along the major axis from the refractive power along the minor axis. The equations set forth in "Photorefractive keratectomy: A technique for laser refractive surgery" authored by Munnerlyn, et al., J. Cataract Refract Surg—Vol. 18, pages 46–52 (Jan., 1988), the disclosure of which is hereby incorporated by reference, can be used to calculate the ablation geometry in corneal tissue along the major and minor axes of the ellipse. Along the major axis, the length of the major axis, $S_{maj}$, is substituted for the treatment diameter, and the dioptric correction entered into the equations is the spherical correction. To determine the ablation geometry along the minor axis, the sum of the spherical and cylindrical corrections is entered into the equations as the dioptric correction, and the length of the minor axis, $S_{min}$, is substituted for the treatment diameter.

The relative sizes of the major and minor axes will depend upon the ratio of cylindrical to spherical correction. Assuming that the length of the major axis is held constant, the length of the minor axis is approximated by $$S_{min} \approx S_{maj}[(D_{cyl}/D_{sph})+1]^{-\frac{1}{2}}.$$

In the above equation, $S_{min}$ is the length of the minor axis, $S_{maj}$ the length of the major axis, $D_{cyl}$ the cylindrical correction and $D_{sph}$ the spherical correction. As noted above, this equation assumes minus notation for the cylindrical portion of the correction.

Figure 4:
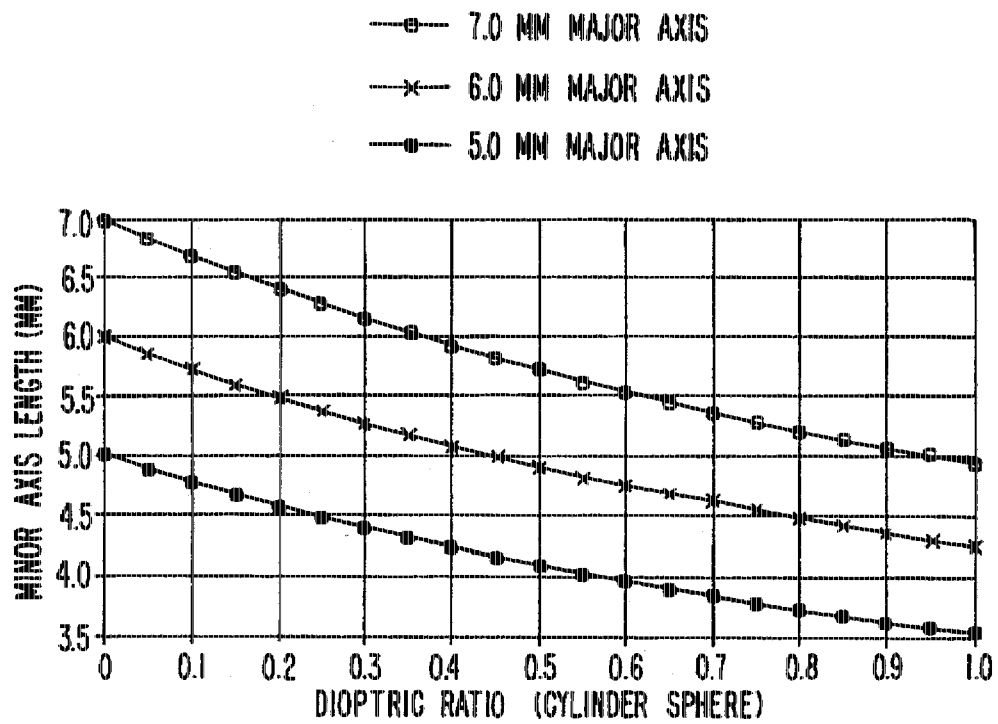
FIG. 4 is a graph showing variation of the minor axis length with correction ratio for different major axis lengths.

To be effective clinically, an elliptical ablation must have a sufficiently large minor axis comparable in size to the maximum diameter of the corneal treatment zone. As shown in FIG. 4, which plots varying ratios of cylindrical to spherical corrections for constant major axis length, there are certain practical limits to the maximum ratio of cylindrical to spherical corrections. In particular, for a given major axis length the length of the minor axis decreases as the ratio of cylindrical to spherical correction increases. For example, for a major axis of 6.0 mm (corresponding to a laser capable of producing a maximum treatment diameter of 6.0 mm), the minor axis for equal spherical and cylindrical corrections is 4.25 mm. This suggests that the clinical use of toric ablations to correct refractive cylinder should be limited to patients having at least as much spherical error as cylindrical error (for a 6.0 mm maximum treatment diameter). For larger maximum treatment diameters (e.g., the upper curve in FIG. 4 corresponding to a 7.0 mm treatment diameter), the ratio constraints will be different.

Returning to FIG. 2, in the preferred embodiment toric ablations are produced by relative motion of the cylinder blades 35, 36 while varying the diameter of the iris 32. Initially, the cylinder blades 35, 36 are completely closed and the iris 32 is opened to the maximum desired diameter. Thereafter, the cylinder blades 35, 36 are progressively opened while the iris 32 is progressively closed by the respective motors 25, 23. As the cylinder blades 35, 36 are opened, the cylindrical component is ablated in the surface of the cornea. As the diameter of iris 32 is closed contemporaneously with the opening of the cylinder blades 35, 36, the spherical component is ablated in the corneal surface. The combined progressive motion of the cylinder blades 35, 36 and the iris 32 produces the toric ablation desired.

As an example, consider the case of a patient with a refraction of −3.0 −2.0×175, average keratometry of 44.5D and a desired 6.0 mm treatment zone. The iris 32 is initially imaged to a 6.0 mm diameter, and cylinder blades 35, 36 are initially placed in the closed position and rotated to the desired angular orientation in the plane of FIG. 2. Thereafter, as laser 28 is pulsed the cylinder blades 35, 36 are progressively opened to effect a −2.0D cylindrical correction. At the same time, iris 32 is progressively closed to effect a −3.0D spherical correction.

The preferred embodiment uses laser 28 to ablate a thin layer of tissue from the surface of the cornea with each pulse. The desired ablation depth along each axis can be predetermined by computer control. The iris 32 is programmed to close at a rate which corresponds to the spherical correction, and the cylindrical blades 35, 36 open at a rate corresponding to the cylindrical correction. The transverse displacement of each aperture between pulses corresponds to the change in desired cut depth for the appropriate aperture (i.e., iris 32 or blades 35, 36). The change in desired cut depth is equal to the amount of material removed with each pulse. Thus, for a −3.0 −2.0×175 correction, the iris 32 is closed to create a −3.0D ablation while the cylinder blades 35, 36 open to create a −2.0D cylindrical correction. Along the minor axis of the ellipse, the combined effect of the iris 32 and cylinder blades 35, 36 produces a −5.0D ablation, while the major axis of the ellipse has a −3.0D ablation.

A significant advantage of the preferred embodiment is that the boundaries of the elliptical ablated area are determined by the combined motion of the iris 32 and the cylinder blades 35, 36. As the simultaneous refractive correction proceeds, the intersection of the cylinder blades and iris mark the outer edge of the ablation. The ratio of the minor to major axes is determined by the relative motion of the iris 32 and the cylinder blades 35, 36. Thus, the exact geometry of the ablated area need not be solved for explicitly, and can be varied depending upon the correction required.

Since the number of laser pulses required to effect the spherical correction will usually be greater than the number of laser pulses required to effect the cylindrical correction (assuming equal treatment values of S in the equations of Munnerlyn et al.), cylinder blades 35, 36 will be fully opened to the 6.0 mm position while the iris 32 is not yet fully closed in the above example. Cylinder blades 35, 36 are left at the 6.0 mm position without further movement while the laser finishes the extra pulses required until iris 32 is fully closed. It should be noted that an alternate method of operating the iris 32 and the cylinder blades 35, 36 is to start with the iris 32 initially closed and the cylinder blades 35, 36 initially opened to the maximum slot width, followed by progressive opening of the iris 32 and progressive closing of the blades 35, 36. If the number of pulses required to effect the spherical correction is greater than that required to effect the cylindrical correction (which will be the case whenever the ratio of cylinder-to-sphere shown in FIG. 4 is less than 1.0 and the programmed treatment diameters are equal), motion of blades 35, 36 must be delayed until the extra number of pulses required for the spherical correction have been produced. Otherwise, the blades 35, 36 will be fully closed before the spherical correction is completed. This alternate method of operation thus requires additional capability in the system of FIG. 1 to delay the operation of the astigmatism motor 25 in the closing direction until the extra number of laser pulses required for the spherical correction have been produced.

While the embodiment employing the iris 32 and cylinder blades 35, 36 described above is preferred, the toric ablation may also be effected by employing a variable aperture laser beam modulator to produce an elliptical beam profile of variable dimensions. This may be done by using a mask rotatably mounted in the beam path and having a plurality of variable dimension elliptical apertures with progressive sizes required to produce the desired toric ablation. Alternatively, the mask may have circular apertures of different diameters, and the mask may be positioned at an angle with respect to the laser beam axis so that each circular aperture provides an elliptical profile to the laser beam. The apertured mask is progressively re-positioned between pulses of the laser beam so as to vary the area of the corneal surface exposed to the laser beam from a smallest elliptical area to a largest elliptical area (or the reverse). Care must be taken to ensure that the major axis of each ellipse is collinear with the desired axis of cylindrical ablation throughout the surgery, and this requires precise positioning of the cornea with respect to the elliptical axes. This alternative embodiment has the advantage of employing apertured masks which may already be present in an existing system, such as those shown in the above-referenced U.S. Pat. No. 4,732,148 (particularly FIGS. 9 and 24).

As will now be apparent, the invention enables both spherical and cylindrical corrections to be concurrently effected to the eye of a patient, thus eliminating the prior need with variable aperture and slit systems to first perform the one type of correction (usually the astigmatic correction using the slit) followed by the other correction (typically the spherical correction using the variable aperture). This reduces the total number of pulses required to effect both types of correction to simply the number required to perform the spherical correction. Since the laser beam cross section and intensity can vary over time and with repeated pulsing, the invention reduces the likelihood of error in effecting the desired contoured shaping of the corneal surface. In addition, by sculpting the corneal surface using a toric ablation, the steep vertical "walls" with depth equal to the astigmatic ablation depth are not formed at each end of the cylindrical ablation; consequently, there is no need to produce the sigmoidal transition zones, which simplifies the procedure. In addition, the absence of any steep edges in the corneal ablation reduces the tendency of the eye to produce excessive growth of the epithelium over the ablated surface and this reduces the hyperopic shift phenomenon.

It is understood that the invention encompasses various techniques used to prepare the anterior surface of the cornea for the laser based ablation. For example, removal of the epithelium by both surgical scraping and peeling to expose the corneal surface, as well as laser ablation of the epithelium prior to or contemporaneously with the laser sculpting of the corneal surface, are encompassed by the invention. Thus, the term "corneal surface" refers to the surface to be sculpted to the desired corrective curvature, regardless of whether or not the epithelium or Bowman's membrane (or both) intervene with the actual corneal surface.

While the above provides a full and complete disclosure of the preferred embodiments of the invention, various modifications, alternate constructions and equivalents may be employed as desired. For example, while the invention has been described with specific reference to the system of FIGS. 1 and 2, other arrangements may be employed to produce the variable rectangular and circular areal irradiation desired. Therefore, the above description and illustrations should not be construed as limiting the invention, which is defined by the appended claims.

What is claimed is:

1. A system for changing the anterior surface the cornea of an eye from an initial spherical and cylindrical curvature having myopic and astigmatic optical properties to a subsequent curvature having correctively improved optical properties, the cornea having a surface and a stroma, the system comprising laser for generating a beam of ultraviolet radiation along a path, and a variable aperture device disposed in the path of said beam for exposing the surface of the cornea and permitting the ultraviolet laser radiation to pass through the variable aperture element to selectively ablate the exposed surface of the cornea by photodecomposition, with penetration into the stroma and simultaneous spherical and cylindrical volumetric sculpturing removal of corneal tissue during at least a portion of the selective ablation to such penetration depth and profile as to characterize the surface of the cornea with said subsequent curvature.

2. The system of claim 1 wherein said variable aperture device comprises a slit of varying width and a diaphragm of varying diameter.

3. The system of claim 1 further comprising a modulator for varying the slit width from a maximum to a minimum value and the aperture diameter from a minimum to a maximum value.

4. The system of claim 1 further comprising a modulator for varying the slit width from a minimum to a maximum value and the aperture diameter from a maximum to a minimum value.

5. The system of claim 4 wherein said modulator produces an elliptical ablation profile of variable dimension.

6. The system of claim 5 wherein the variable aperture device is provided with a plurality of circular apertures; and wherein the modulator includes means for angularly directing the laser beam at the variable aperture element and means for progressively positioning different ones of the circular apertures in the path of the beam.

7. A method of changing the anterior surface of the cornea of an eye from an initial spherical and cylindrical curvature having myopic and astigmatic optical properties to a subsequent curvature having correctively improved optical properties, the cornea having a stroma, which method comprises exposing the anterior surface of the cornea and permitting ultraviolet laser radiation to pass through a variable aperture element to selectively ablate the exposed anterior surface of the cornea by photodecomposition, with penetration into the stroma and simultaneous spherical and cylindrical volumetric sculpting removal of corneal tissue during at least a portion of the selective ablation to such penetration depth and profile as to characterize the anterior surface of the cornea with said subsequent curvature.

8. The method of claim 7 wherein said step of using includes the step of selectively irradiating the corneal surface by passing a laser beam along a path through a variable aperture laser beam modulator to produce an elliptical beam profile of variable dimensions.

9. The method of claim 8 wherein the elliptical beam profile is produced by angularly directing the laser beam at a variable aperture element having a plurality of circular apertures and progressively positioning different ones of the apertures into the path of the beam.

10. The method of claim 7 wherein said step of permitting includes the step of selectively irradiating the corneal surface by passing a laser beam through a slit of varying width and an aperture of varying diameter.

11. The method of claim 10 wherein said step of passing includes the steps of varying the slit width from a minimum to a maximum value and varying the aperture diameter from a maximum to a minimum value.

12. The method of claim 10 wherein said step of passing includes the steps of varying the slit width from a maximum to a minimum value and varying the aperture diameter from a minimum to a maximum value.

* * * * *